US010921958B2

United States Patent
Lee et al.

(10) Patent No.: US 10,921,958 B2
(45) Date of Patent: Feb. 16, 2021

(54) ELECTRONIC DEVICE SUPPORTING AVATAR RECOMMENDATION AND DOWNLOAD

(71) Applicant: Samsung Electronics Co., Ltd., Gyeonggi-do (KR)

(72) Inventors: Wooyong Lee, Gyeonggi-do (KR); Junyoung Park, Gyeonggi-do (KR); Myunghan You, Gyeonggi-do (KR); Jungeun Lee, Gyeonggi-do (KR); Inho Jeong, Gyeonggi-do (KR); Chanmin Park, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 16/747,936

(22) Filed: Jan. 21, 2020

(65) Prior Publication Data
US 2020/0264738 A1    Aug. 20, 2020

(30) Foreign Application Priority Data
Feb. 19, 2019    (KR) .......................... 10-2019-0019117

(51) Int. Cl.
*G06F 3/048*    (2013.01)
*G06F 3/0482*   (2013.01)
(Continued)

(52) U.S. Cl.
CPC ........ *G06F 3/0482* (2013.01); *G06F 3/04817* (2013.01); *G06F 3/04842* (2013.01); *G06T 11/00* (2013.01); *G06T 2200/24* (2013.01)

(58) Field of Classification Search
CPC ............. G06F 3/04817; G06F 3/04842; G06F 3/0482; G06T 2200/24; G06T 11/00
See application file for complete search history.

(56) References Cited

U.S. PATENT DOCUMENTS

2007/0078993 A1* 4/2007 Issa .................... H04N 21/4825
                                                        709/229
2010/0026698 A1    2/2010 Reville et al.
(Continued)

FOREIGN PATENT DOCUMENTS

WO    2009/133710 A1    11/2009

OTHER PUBLICATIONS

International Search Report dated Apr. 17, 2020.
European Search Report dated Jun. 26, 2020.

*Primary Examiner* — Pei Yong Weng
(74) *Attorney, Agent, or Firm* — Cha & Reiter, LLC.

(57) ABSTRACT

An electronic device and method are disclosed. The electronic device includes: an input circuitry, a display, a camera, a communication circuitry, a processor operatively connected to the input circuitry, the display, the camera, and the communication circuitry, and a memory operatively connected to the processor. The processor implements the method, including display, on the display, one or more images depicting characters selectable as avatars, detect via the input circuitry a selection of a character as an avatar, set the selected character as the avatar, replacing an object included in an image captured by the camera, and display, on the display, one or more icons representing one or more packages including a first package associated with the selected character, based on identification information for the selected character.

20 Claims, 11 Drawing Sheets

(51) Int. Cl.
    *G06F 3/0481*     (2013.01)
    *G06F 3/0484*     (2013.01)
    *G06T 11/00*     (2006.01)

(56) References Cited

U.S. PATENT DOCUMENTS

| | | |
|---|---|---|
| 2010/0121915 A1 | 5/2010 | Wang |
| 2010/0199200 A1 | 8/2010 | Fujioka |
| 2011/0060988 A1* | 3/2011 | Mysliwy ............... G06F 3/0482 715/702 |
| 2012/0265602 A1 | 10/2012 | Corner et al. |
| 2013/0047084 A1* | 2/2013 | Sanders ............. G06F 16/4387 715/716 |
| 2014/0082497 A1* | 3/2014 | Chalouhi ............. G06F 16/447 715/716 |
| 2015/0312523 A1 | 10/2015 | Li et al. |
| 2016/0361653 A1 | 12/2016 | Zhang et al. |
| 2017/0312634 A1 | 11/2017 | Ledoux et al. |
| 2018/0198744 A1 | 7/2018 | Ziglar et al. |
| 2018/0336716 A1 | 11/2018 | Ramprashad et al. |
| 2019/0342507 A1* | 11/2019 | Dye ....................... G06F 3/017 |

\* cited by examiner

ELECTRONIC DEVICE SUPPORTING AVATAR RECOMMENDATION AND DOWNLOAD

CROSS-REFERENCE TO RELATED APPLICATION

This application is based on and claims priority under 35 U.S.C. § 119 to Korean Patent Application No. 10-2019-0019117, filed on Feb. 19, 2019, in the Korean Intellectual Property Office, the disclosure of which is incorporated by reference herein in its entirety.

BACKGROUND

Field

Certain embodiments of the disclosure relate to an electronic device capable of recommending and downloading a character suitable as an avatar of the user and/or an accessory to be applied to the avatar.

Description of Related Art

An electronic device may generate a visual avatar representative of the user, by applying visual processes to an image of the user captured by a camera, or may receive various avatar-style characters selectable for use as a user avatar from external sources accessed through the network. The electronic device may provide various services using the avatar, such as games in which the user is represented by the avatar, social media services or messenger services in which the user is identified by the avatar.

SUMMARY

'Characters' may be packaged and provided through an application store (e.g., Galaxy Apps™). 'Characters' may indicate a persona and/or fictitious entity, person, animal, etc., such as a persona/character presented in media, such as movies, television shows, animations, etc. Nowadays, such characters may be desirable for use as user avatars in a digital context, like an avatar service. The electronic device may access an online store through a network, download a package corresponding to a desired character as selected by the user, and install the package in the memory. However, in providing the avatar service to the user, associations between packages, characters and/or decorative accessories for use with avatars is not often considered. Hence, it is difficult to provide the user with a service that enables selection and recommendation of packages and accessories suitable and/or compatible with a given character.

Accordingly, certain embodiments of the disclosure provides an electronic device that can recommend a downloadable package associated with a character based on designated character information to thereby provide the user with convenience of searching and enhance the utilization of an avatar service.

According to certain embodiments of the disclosure, there is provided an electronic device, which may include: an input circuitry, a display, a camera, a communication circuitry, a processor operatively connected to the input circuitry, the display, the camera, and the communication circuitry, and a memory operatively connected to the processor, wherein the memory stores instructions that, when executed, cause the processor to: display, on the display, one or more images depicting characters selectable as avatars, detect via the input circuitry a selection of a character as an avatar, set the selected character as the avatar, replacing an object included in an image captured by the camera, and display, on the display, one or more icons representing one or more packages including a first package associated with the selected character, based on identification information for the selected character.

According to certain embodiments of the disclosure, there is provided a method, which may include: displaying, on a display, one or more images depicting characters selectable as avatars, detecting, using input circuitry, a selection of a character from among the one or more images as an avatar, setting, by a processor, the selected character as the avatar by replacing an object included in an image captured by a camera of the electronic device, and displaying, on the display, one or more icons representing one or more packages including a first package associated with the selected character, based on identification information for the selected character. The instructions may cause the processor to download the first package from an external electronic device through the communication module based on receiving a user input to the first package icon from the input device or the display.

When the first package has been downloaded and installed in the memory, the instructions may cause the processor to: find a second package flag included in the character from the memory based on the character being displayed in place of the object; recognize that the first package includes a flag identical to the second package flag; and display, based on the recognition, information about the first package together with the character on the display.

Certain embodiments of the disclosure may provide the user with the convenience of searching for an avatar package, thereby enhancing the utilization of the avatar service.

BRIEF DESCRIPTION OF THE DRAWINGS

The above and other aspects, features and advantages of certain embodiments of the present disclosure will be more apparent from the following detailed description, taken in conjunction with the accompanying drawings, in which.

DETAILED DESCRIPTION

Figure 1:
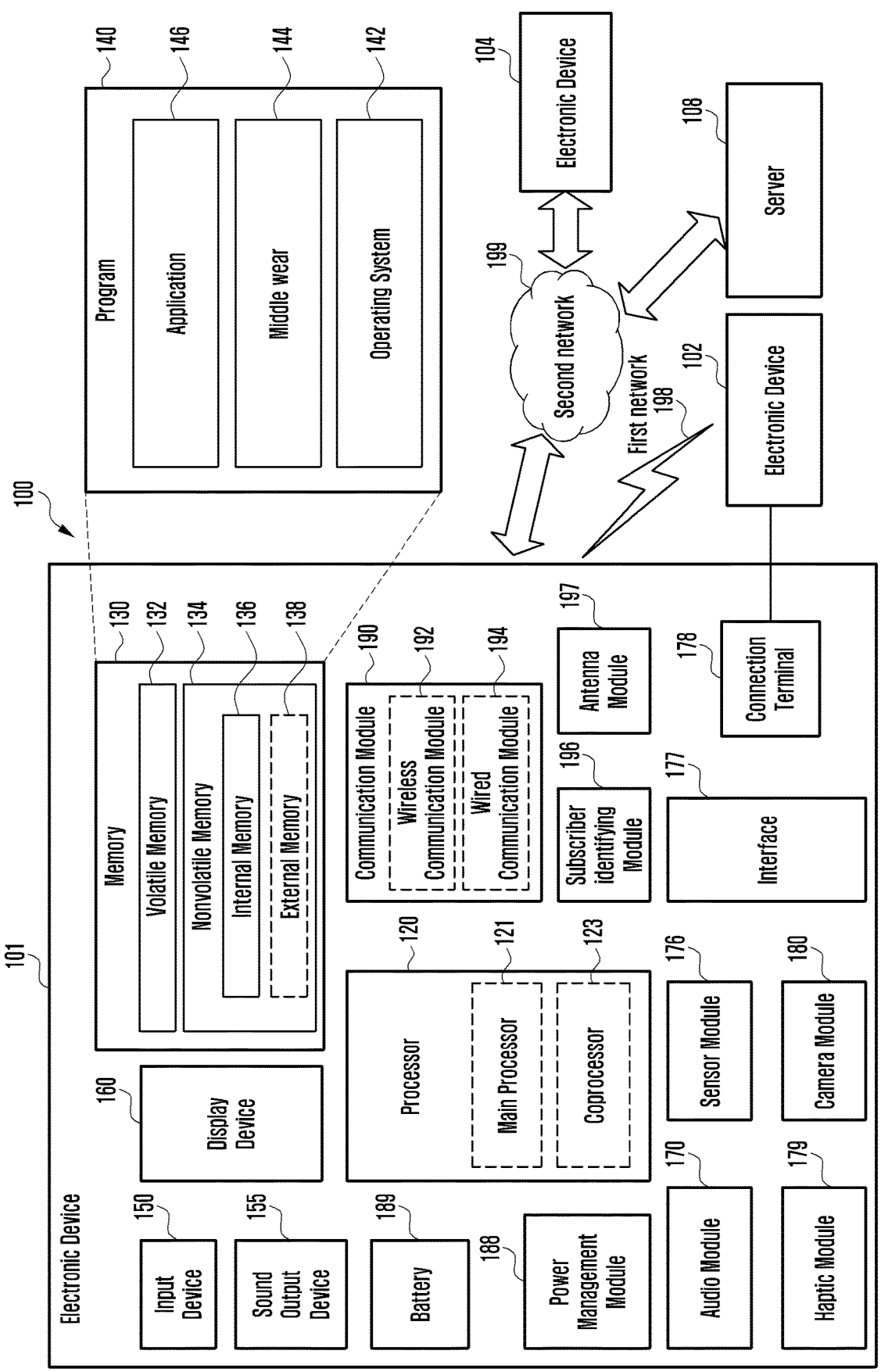
FIG. 1 is a block diagram of an electronic device in a network environment according to certain embodiments.

FIG. 1 is a block diagram illustrating an electronic device 101 in a network environment 100 according to certain embodiments. Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to an embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related therereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse, a keyboard, or a digital pen (e.g., a stylus pen).

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry (or touch input circuitry) adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to an embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include an antenna including a radiating element implemented by a conductive material or a conductive pattern formed in or on a substrate (e.g., PCB). According to an embodiment, the antenna module 197 may include a plurality of antennas. In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

Figure 2:
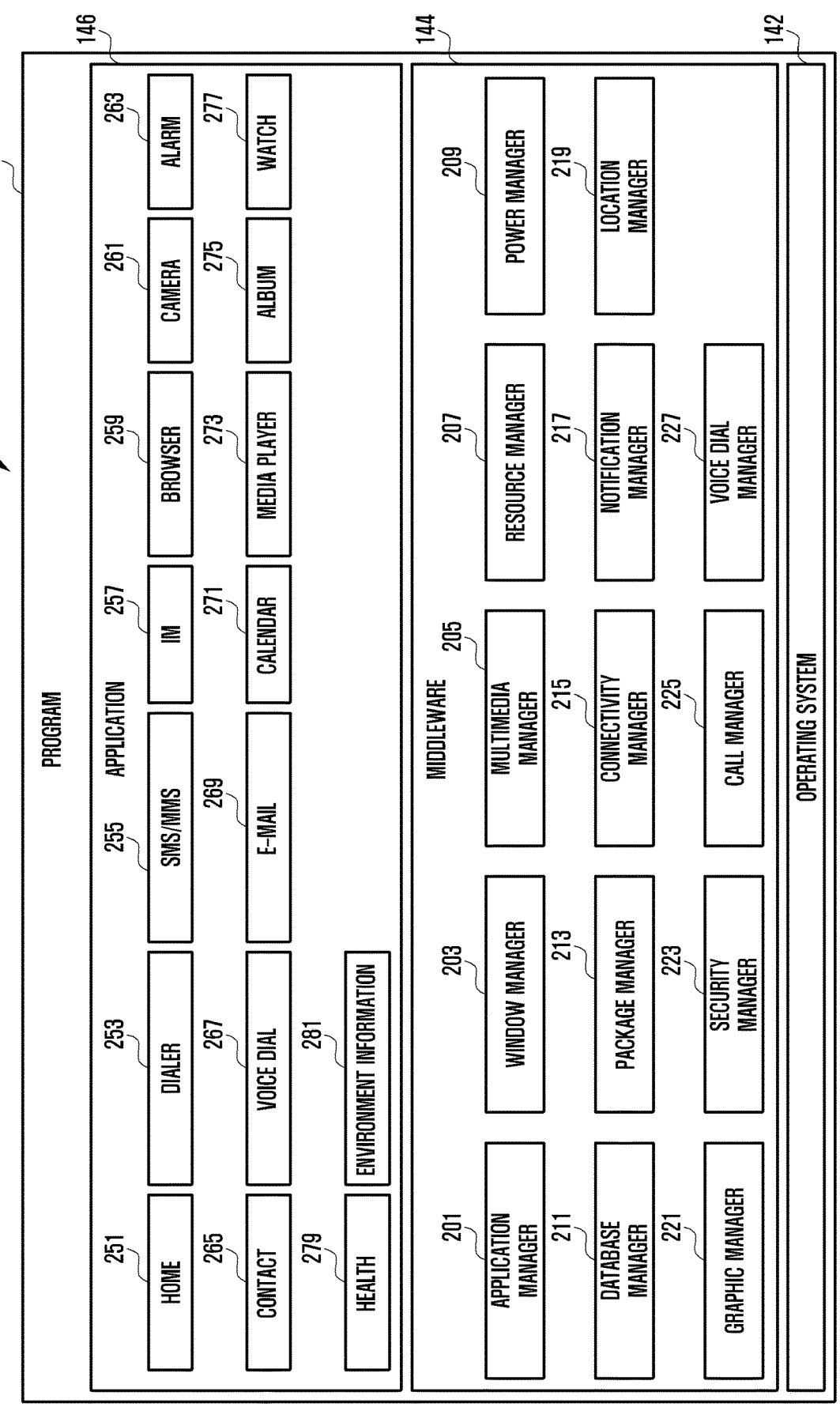
FIG. 2 illustrates a structure of programs according to certain embodiments.

FIG. 2 is a block diagram 200 illustrating the program 140 according to certain embodiments. According to an embodiment, the program 140 may include an operating system (OS) 142 to control one or more resources of the electronic device 101, middleware 144, or an application 146 executable in the OS 142. The OS 142 may include, for example, Android™, iOS™, Windows™, Symbian™, Tizen™, or Bada™. At least part of the program 140, for example, may be pre-loaded on the electronic device 101 during manufacture, or may be downloaded from or updated by an external electronic device (e.g., the electronic device 102 or 104, or the server 108) during use by a user.

The OS 142 may control management (e.g., allocating or deallocation) of one or more system resources (e.g., process, memory, or power source) of the electronic device 101. The OS 142, additionally or alternatively, may include one or more driver programs to drive other hardware devices of the electronic device 101, for example, the input device 150, the sound output device 155, the display device 160, the audio module 170, the sensor module 176, the interface 177, the haptic module 179, the camera module 180, the power management module 188, the battery 189, the communication module 190, the subscriber identification module 196, or the antenna module 197.

The middleware 144 may provide various functions to the application 146 such that a function or information provided from one or more resources of the electronic device 101 may be used by the application 146. The middleware 144 may include, for example, an application manager 201, a window manager 203, a multimedia manager 205, a resource manager 207, a power manager 209, a database manager 211, a package manager 213, a connectivity manager 215, a notification manager 217, a location manager 219, a graphic manager 221, a security manager 223, a telephony manager 225, or a voice recognition manager 227.

The application manager 201, for example, may manage the life cycle of the application 146. The window manager 203, for example, may manage one or more graphical user interface (GUI) resources that are used on a screen. The multimedia manager 205, for example, may identify one or more formats to be used to play media files, and may encode or decode a corresponding one of the media files using a codec appropriate for a corresponding format selected from the one or more formats. The resource manager 207, for example, may manage the source code of the application 146 or a memory space of the memory 130. The power manager 209, for example, may manage the capacity, temperature, or power of the battery 189, and determine or provide related information to be used for the operation of the electronic device 101 based at least in part on corresponding information of the capacity, temperature, or power of the battery 189. According to an embodiment, the power manager 209 may interwork with a basic input/output system (BIOS) (not shown) of the electronic device 101.

The database manager 211, for example, may generate, search, or change a database to be used by the application 146. The package manager 213, for example, may manage installation or update of an application that is distributed in the form of a package file. The connectivity manager 215, for example, may manage a wireless connection or a direct connection between the electronic device 101 and the external electronic device. The notification manager 217, for example, may provide a function to notify a user of an occurrence of a specified event (e.g., an incoming call, message, or alert). The location manager 219, for example, may manage locational information on the electronic device 101. The graphic manager 221, for example, may manage one or more graphic effects to be offered to a user or a user interface related to the one or more graphic effects.

The security manager 223, for example, may provide system security or user authentication. The telephony manager 225, for example, may manage a voice call function or a video call function provided by the electronic device 101. The voice recognition manager 227, for example, may transmit a user's voice data to the server 108, and receive, from the server 108, a command corresponding to a function to be executed on the electronic device 101 based at least in part on the voice data, or text data converted based at least in part on the voice data. According to an embodiment, the middleware 244 may dynamically delete some existing components or add new components. According to an embodiment, at least part of the middleware 144 may be included as part of the OS 142 or may be implemented as another software separate from the OS 142.

The application 146 may include, for example, a home 251, dialer 253, short message service (SMS)/multimedia messaging service (MMS) 255, instant message (IM) 257, browser 259, camera 261, alarm 263, contact 265, voice recognition 267, email 269, calendar 271, media player 273, album 275, watch 277, health 279 (e.g., for measuring the degree of workout or biometric information, such as blood sugar), or environmental information 281 (e.g., for measuring air pressure, humidity, or temperature information) application. According to an embodiment, the application 146 may further include an information exchanging application (not shown) that is capable of supporting information exchange between the electronic device 101 and the external electronic device. The information exchange application, for example, may include a notification relay application adapted to transfer designated information (e.g., a call, message, or alert) to the external electronic device or a device management application adapted to manage the external electronic device. The notification relay application may transfer notification information corresponding to an occurrence of a specified event (e.g., receipt of an email) at another application (e.g., the email application 269) of the electronic device 101 to the external electronic device. Additionally or alternatively, the notification relay application may receive notification information from the external electronic device and provide the notification information to a user of the electronic device 101.

The device management application may control the power (e.g., turn-on or turn-off) or the function (e.g., adjustment of brightness, resolution, or focus) of the external electronic device or some component thereof (e.g., a display device or a camera module of the external electronic device). The device management application, additionally or alternatively, may support installation, delete, or update of an application running on the external electronic device.

The electronic device according to certain embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that certain embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Certain embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. The term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to certain embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to certain embodiments, each component (e.g., a module or a program) of the above-described components may include a single entity or multiple entities. According to certain embodiments, one or more of the above-described components may be omitted, or one or more other components may be added. Alternatively or additionally, a plurality of components (e.g., modules or programs) may be integrated into a single component. In such a case, according to certain embodiments, the integrated component may still perform one or more functions of each of the plurality of components in the same or similar manner as they are performed by a corresponding one of the plurality of components before the integration. According to certain embodiments, operations performed by the module, the program, or another component may be carried out sequentially, in parallel, repeatedly, or heuristically, or one or more of the operations may be executed in a different order or omitted, or one or more other operations may be added.

Figure 3:
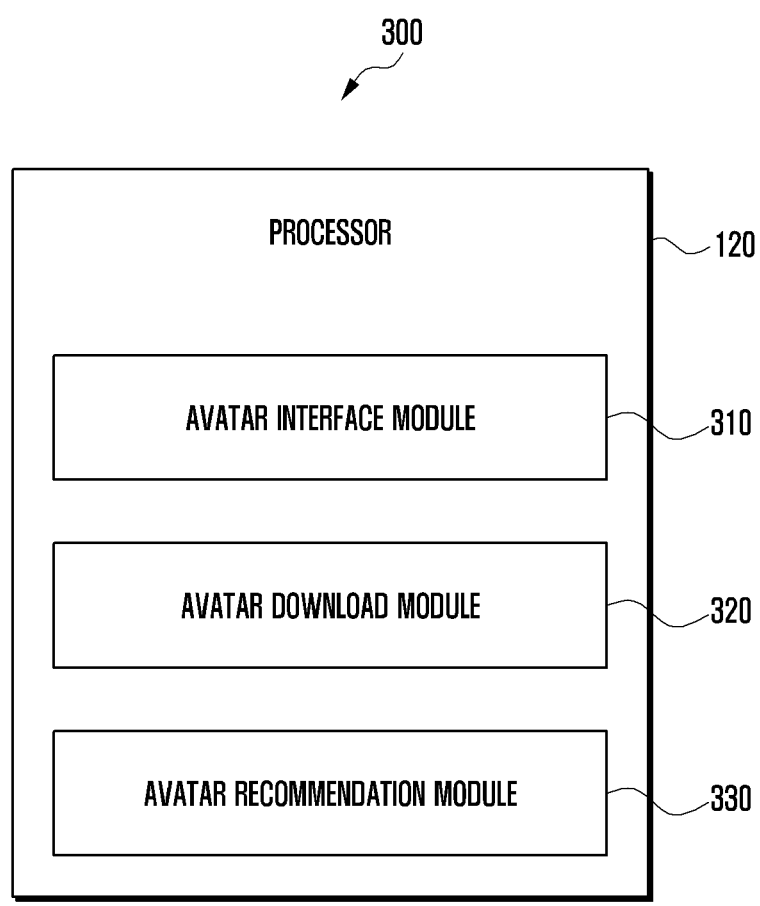
FIG. 3 is a block diagram of a processor according to certain embodiments.

FIG. 3 is a block diagram 300 of the processor 120 according to certain embodiments. With reference to FIG. 3, the processor 120 may include an avatar interface module 310, an avatar download module 320, and an avatar recommendation module 330. The above modules 310, 320 and 330 may be configured as hardware modules of the processor 120 (e.g., main processor 121 or secondary processor 123). The modules 310, 320 and 330 may be implemented in software (e.g., programs 140), and, when executed, instructions of the corresponding module may be executed by the processor 120 (e.g., main processor 121 and/or secondary processor 123).

In certain embodiments, the avatar interface module 310 may provide a user interface environment through the display device 160 (e.g., touchscreen display including a touch circuit) to support functions related to an avatar (e.g., augmented reality (AR) avatar). For example, avatar-related functions may include: recognizing an object (e.g., user) in an image, generating an avatar to represent the object, applying the avatar to the object (e.g., displaying the avatar in replacement of the face), downloading an avatar (e.g., character (e.g., hero of an animated movie) or an accessory to decorate it), and selecting an accessory suitable for a specified character (e.g., character selected or displayed by the user) and recommending the same to the user.

In an embodiment, when an image (or, corresponding low resolution image) obtained through the camera module 180 is displayed (e.g., previewed) in response to the execution of the camera application 261, the avatar interface module 310 may also display a first item (e.g., icon) for entering avatar camera mode (in other words, avatar camera menu) on the display device 160. The avatar interface module 310 may recognize a user selection (e.g., touch on the corresponding item) for the first item. Upon recognizing a user selection for the first item, the avatar interface module 310 may display an avatar camera menu along with the preview image (e.g., preview image at the top of the screen and avatar camera menu at the bottom of the screen) to support an avatar-related function (e.g., creating an avatar, downloading an avatar, detecting an object in an image, or displaying an avatar in replacement of an object). The above function may be provided as one of the functions provided by the camera application 261 (also known as "app in app").

In an embodiment, when the preview image is displayed, the avatar interface module 310 may also display a second item (e.g., icon) on the display device 160 for entering avatar home mode (in other words, avatar home screen or avatar showroom). Avatar home mode may support a hub function such as displaying an image in the showroom, causing the avatar displayed in the showroom to perform a specific action according to a user input (e.g., giving a greeting upon touching the avatar's hand), avatar editing, background editing, sticker management (e.g. create, edit, or download a sticker), or sharing with another tool (e.g. sharing an avatar with another application). For example, the second item may be displayed together with the first item. As another example, the second item may be displayed as a part of the avatar camera menu. The avatar interface module 310 may recognize a user selection (e.g., touching the corresponding item) for the second item. Upon recognizing a user selection for the second item, the avatar interface module 310 may end the display of the preview image and perform a function of avatar home mode. This function may be provided as a separate independent application instead of a module in the camera application 261. Hence, the processor 120 may provide an image home screen based on a user input (e.g., user voice input from the microphone, or hand touch input (or pen touch input) to the avatar home icon on the display) without executing the camera application 261.

In certain embodiments, the avatar download module 320 may access an avatar providing server (e.g., server 108 in FIG. 1) through the communication module 190, and may download a package (e.g., character package, or accessory package including accessories for decorating at least one character of the character package) from the server based on a user input through the avatar camera menu or the avatar home screen.

In certain embodiments, the avatar recommendation module 330 may perform an accessory recommendation function for the user by displaying an accessory (and/or character) suitable for a designated character (e.g., character selected or displayed by the user in avatar camera mode or avatar home mode) first among the downloaded accessories.

Figure 4:
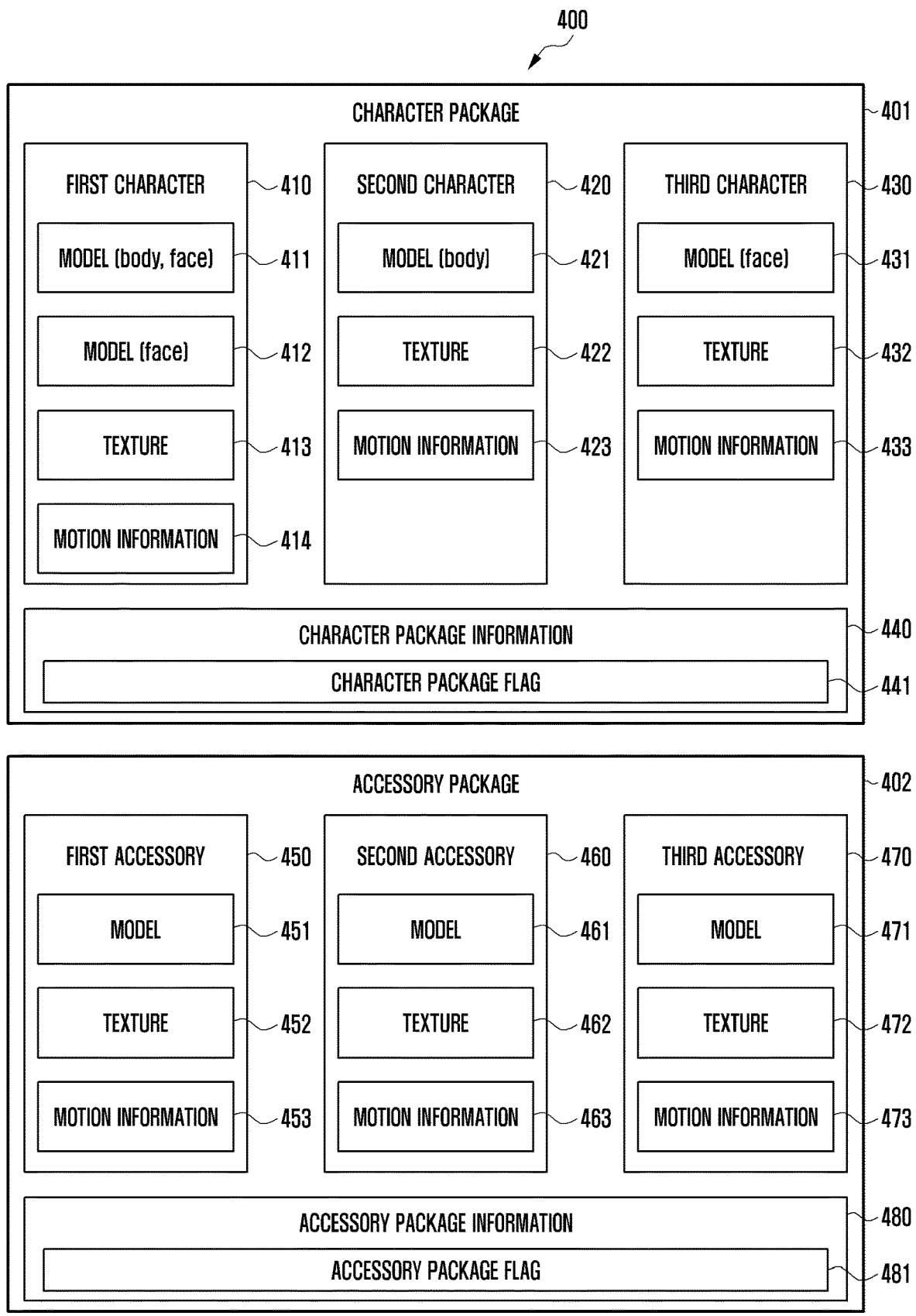
FIG. 4 illustrates a package data structure according to certain embodiments.

FIG. 4 illustrates a package data structure 400 according to certain embodiments. With reference to FIG. 4, the processor 120 (e.g., avatar download module 320) may download a character package 401 and/or an accessory package 402 from the server through the communication module 190 and install the downloaded package in the memory 130.

In certain embodiments, the character package 401 may include a plurality of characters (e.g., first character 410, second character 420, and third character 430) and character package information 440. Each character may include a three-dimensional model, a texture (e.g., image used to represent the color or texture of the corresponding three-dimensional model), and motion (gesture) information. For example, the first character 410 may include a three-dimensional model 411 to be applied to the body and face of an object, a three-dimensional model 412 to be applied to the face of the object, a texture 413, and motion information 414. The second character 420 may include a body model 421, a texture 422, and motion information 423. The third character 430 may include a face model 431, a texture 432, and motion information 433.

In certain embodiments, the character package information 440 may include a character package flag 441. The character package flag 441 may include various identifying information for the corresponding package and/or a character belonging thereto. In an embodiment, the character package flag 441 may include identification information of the corresponding character package (e.g., title, uniform resource identifier (URI), or identifier (ID) of a movie in which the characters 410, 420 and 430 appear), identification information of each character (e.g., name of the character in the movie), identification information of the character (or package) holder, or identification information of the content provider having obtained a license of the character (or package) from the holder. For example, the flag of the character package 401 may include identification information of the corresponding character package (e.g., SAMSUNG Emoji) or identification information of the holder (e.g., Samsung Electronics). In the character package 401, the flag of each character may include the name of the character. A 'flag' may thus be understood as any suitable type of metadata that provides this identifying and/or matching function between characters, accessories, and other effects desirable for incorporation into the presentation of avatars in a digital context.

In certain embodiments, the accessory package 402 may include a plurality of accessories (e.g., first accessory 450, second accessory 460, and third accessory 470) and accessory package information 480. Each accessory can include a three-dimensional model, a texture, and motion information. For example, the first accessory 450 (e.g., hat) can include a three-dimensional model 451 representing its appearance, a texture 452, and motion information 453. The second accessory 460 (e.g., glasses) can include a three-dimensional model 461, a texture 462, and motion information 463. The third accessory 470 (e.g., shoes) can include a three-dimensional model 471, a texture 472, and motion information 473.

In certain embodiments, the accessory package information 480 may include an accessory package flag 481. The accessory package flag 481 may include various information for identifying the corresponding package and/or an accessory belonging thereto. In an embodiment, the accessory package flag 481 may include identification information of the corresponding accessory package (e.g., type (e.g., costume set), URI, or ID of the accessory package), identification information for each accessory (e.g., accessory name), identification information of characters to be decorated by the accessories 450, 460 and 460, identification information of the package to which the character to be decorated belongs, identification information of the holder of the character (or package) to be decorated, or identification information of the content provider having obtained a license of the character (or package) to be decorated from the holder. For example, the flag of the accessory package 402 may include identification information of the corresponding accessory package (e.g., costume set), identification information of the character package including the character to be decorated (e.g. SAMSUNG Emoji), or identification information of the character package holder (e.g., Samsung Electronics). In the accessory package 402, the flag of each accessory may include identification information of the accessory (e.g., hat) or identification information of a character to be decorated (e.g., name).

In certain embodiments, the processor 120 (e.g., avatar recommendation module 330) may recognize an association between the characters 410, 420 and 430 and the accessories 450, 460 and 470 based on the package flags 441 and 481. Based on this recognition, the processor 120 may first display the accessories associated with the designated character (e.g., unassociated accessories are not displayed). This flag may be data added to the corresponding package during packaging after having obtained the right to link to the package through licensing or other means and having produced the avatar.

Figure 5:
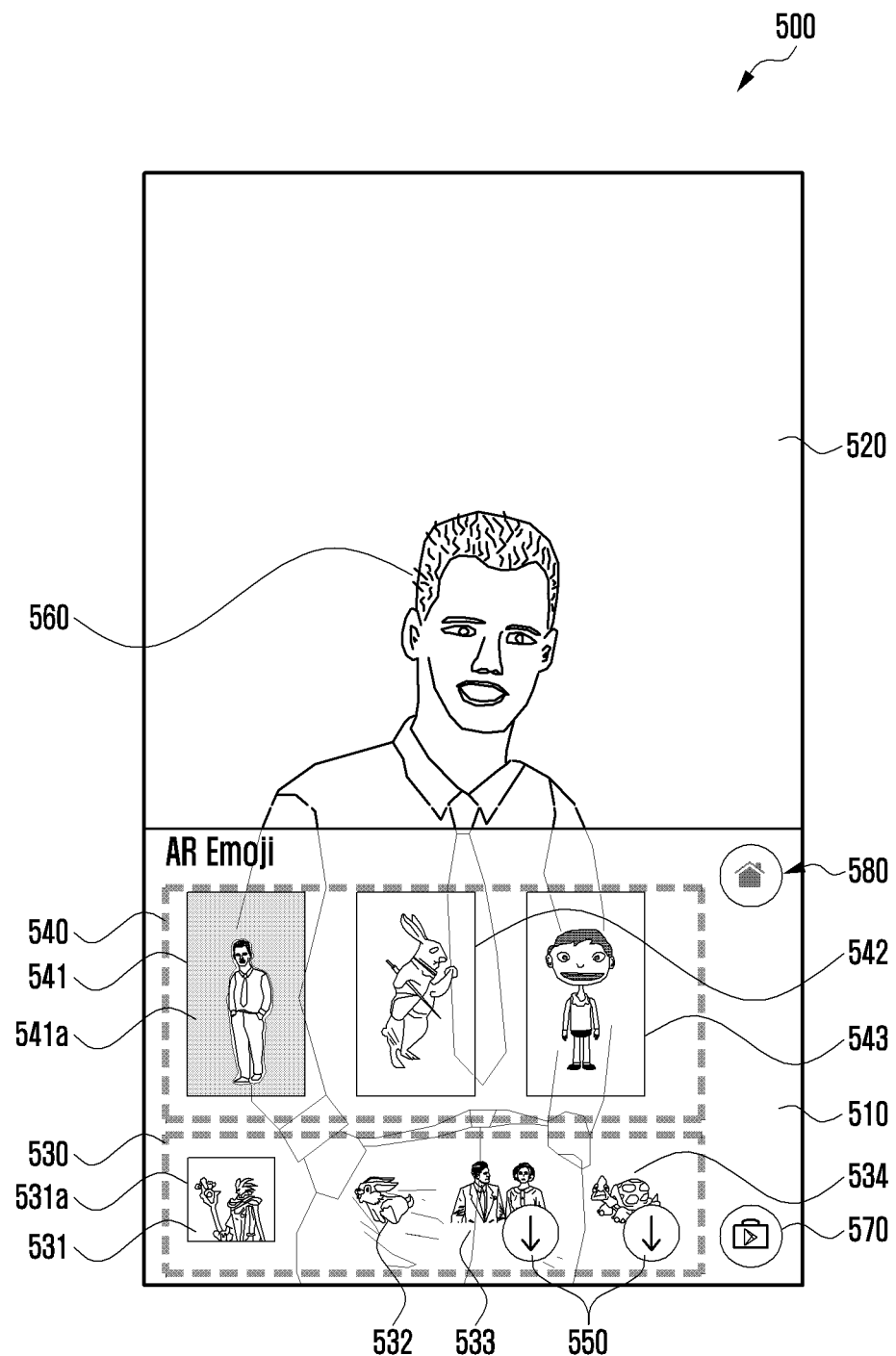
FIG. 5 illustrates a user interface screen supporting display of a downloadable package in avatar camera mode according to certain embodiments.

FIG. 5 illustrates a user interface screen 500 supporting display of a downloadable package, in an avatar camera mode (e.g., Samsung "AR Emoji") according to certain embodiments. With reference to FIG. 5, upon executing the avatar camera mode, the processor 120 may display an avatar camera menu 510 on the preview image 520, to support one or more avatar-related functions.

The processor 120 may display a package list 530 in the avatar camera menu 510. The package list 530 may include a plurality of package icons. For example, the processor 120 may display icons (e.g., first package icon 531 and second package icon 532) for downloaded packages (e.g., character package and/or accessory package) in the package list 530.

The processor 120 may display the icons (e.g., third package icon 533 and fourth package icon 534) of downloadable packages (e.g., character package and/or accessory package) related to the package selected by a user input (e.g., touch on the corresponding icon), among the package icons 531 and 532, in the package list 530.

For example, the processor 120 may receive a selection of the first package icon 531 through the display (e.g., by touch input selection). The processor 120 may retrieve the flag (e.g., Samsung Electronics) of the package (e.g., character package or accessory package) corresponding to the selected first package icon 531 from the memory 130. The processor 120 may generate a request for information about the related package by transmitting the found flag to the server through the communication module 190. The processor 120 may receive package information (e.g., flag and representative image of a package) from the server, and may display the third package icon 533 and the fourth package icon 534, as visual elements of the package list 530 on the display, based on the received package information (e.g., representative image).

As another example, the processor 120 may receive information (e.g., flag and representative image of a package) about a plurality of downloadable packages (e.g., packages related to Samsung Electronics and other packages) in advance (e.g., before entering avatar camera mode, or before receiving a user input for selecting the first package icon 531). The processor 120 may find a flag (e.g., Samsung Electronics) of the package corresponding to the selected first package icon 531 from the memory 130. The processor 120 may identify a downloadable package (e.g., package (s) having a flag of Samsung Electronics) having the same flag as the found flag based on the received package information. The processor 120 may display the icon of the identified downloadable package (e.g., third package icon 533 or fourth package icon 534) as an element of the package list 530 on the display.

As a result, the processor 120 may provide the avatar camera menu 510 as an interface environment supporting avatar download to the user while the camera application 261 is running without entering an application store (e.g. Galaxy Apps™) and without interrupting the user experience with the avatar.

In response to a user input for selecting a package icon (e.g., first package icon 531), as shown in FIG. 5, the processor 120 may display, for example, a square box 531*a* surrounding the first package icon 531 as a visual indication that the first package icon 531 is selected.

The processor 120 may display an indication for distinguishing between the icon of a downloaded package and the icon of a package not downloaded. For example, the processor 120 may attach a mark 550 of a downward arrow shape to the third package icon 533 and the fourth package icon 534 in the package list 530 to indicate that the corresponding package is downloadable.

The processor 120 may exclude an icon of a package that is downloadable but not related to the selected package from the package list 530. For example, a fifth package icon (not shown) may be not included in the package list 530 because the flag of the corresponding package is not the same as the flag of the selected package.

The processor 120 may display the icon of a package related to the selected package first and then display the icon of a package that is downloadable but not related to the selected package. For example, the processor 120 may divide the package list 530 into several pages and display the icons 531, 532, 533 and 534 on the first page. The processor 120 may include the icon of an unrelated package in the second page instead of the first page based on a user input (e.g., touch gesture (e.g., drag) on the first page).

The processor 120 may display a character list 540 in the avatar camera menu 510. For example, in response to a user input for selecting the icon of a downloaded package (e.g., first package icon 531) in the package list 530, the processor 120 may display the icons of characters included in the selected package (e.g., first character icon 541, second character icon 542, or third character icon 543), for example, as a thumbnail in the character list 540.

The processor 120 may track a change in facial expression or gesture of an object (e.g., user) in an image obtained by using the camera module 180. Based on the tracking, the processor 120 may perform an image processing operation (e.g., 3D modeling) on the character corresponding to the character icon selected by the user (e.g., first character icon 541) in the character list 540, and may display the image-processed character in the preview image 520 as an avatar 560 of the object.

The processor 120 may perform an image processing operation on the background 541*a* of the selected character icon (e.g., first character icon 541) so that it differs, for example, in shade or color from the background of other character icons 542 and 543, thus visually distinguishing between the selected character icon and other character icons.

The processor 120 may include an icon 570 for additional package download in the avatar camera menu 510 displayed on the display. In response to a user input for selecting the icon 570, the processor 120 may terminate the display of the avatar camera menu 510 and the preview image 520, and may download a package list from the application store (e.g., Galaxy Apps™) through the communication module 190 and display the downloaded package list on the display.

The processor 120 may display an icon 580 for entering avatar home mode in the avatar camera menu 510. In response to a user input for selecting the icon 580, the processor 120 may terminate the display of the avatar camera menu 510 and the preview image 520, and may display the avatar home screen (not shown) on the display.

Figure 6:
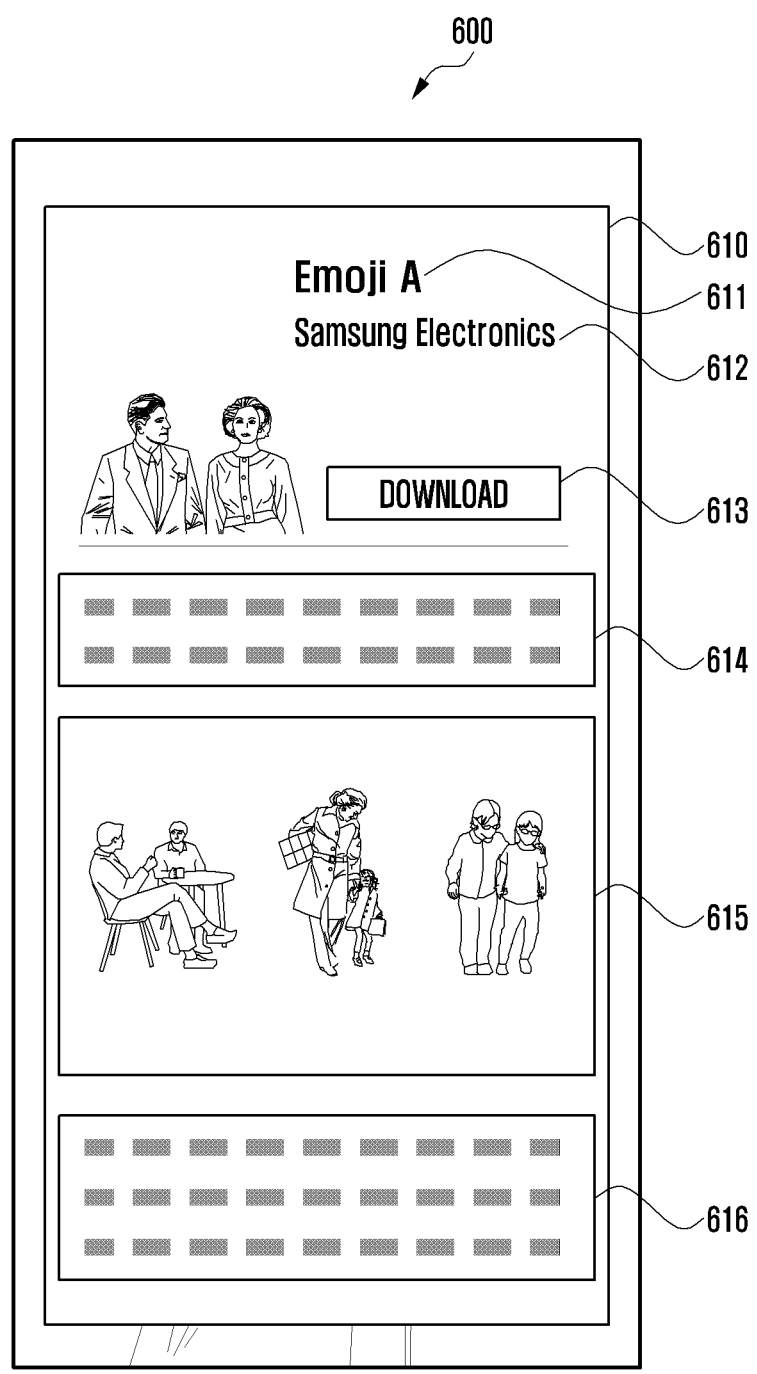
FIG. 6 illustrates a user interface screen supporting download of a selected package according to certain embodiments.

FIG. 6 illustrates a user interface screen 600, that supports download of a selected package according to certain embodiments. With reference to FIG. 6, the processor 120 may display a download window 610 for supporting download of a package, as selected by the user in the avatar camera mode or the avatar home mode. For example, in response to a user input selecting an icon corresponding to a downloadable package (e.g., third package icon 533 in FIG. 5), the processor 120 may display the download window 610 in the preview image (e.g., preview image 520 in FIG. 5). As another example, the processor 120 may display a selected character (e.g., avatar 560 in FIG. 5) on the avatar home screen (which is not shown). The processor 120 may display the icon (e.g., third package icon 533 or fourth package icon 534 in FIG. 5) of a downloadable package (e.g., character packages and/or accessory package) related to the package of the character being displayed on the display. In response to selection of an icon, the processor 120 may display the download window 610 for downloading the corresponding package on the avatar home screen.

The processor 120 may display information about a package to be downloaded (e.g., character package or accessory package) through the download window 610. For example, the processor 120 may generate a request for detailed information on a package to be downloaded, by transmitting package information (e.g., URL or ID) to the server requesting the same. After receiving the detailed information from the server, the processor 120 may generate a download window 610 including a package name 611, a content provider 612, a download button 613, a summary description 614, an overview 615 of the avatar (e.g., character or accessory) included in the package, and a detailed description 616 thereon, and display the download window 610 on the display.

Based on a user's download request (e.g. touch selection of the download button 613), the processor 120 may download the corresponding package from the server. The processor 120 may notify the download status to the user by removing the download button 613 and displaying a download progress bar (not shown).

Figure 7:
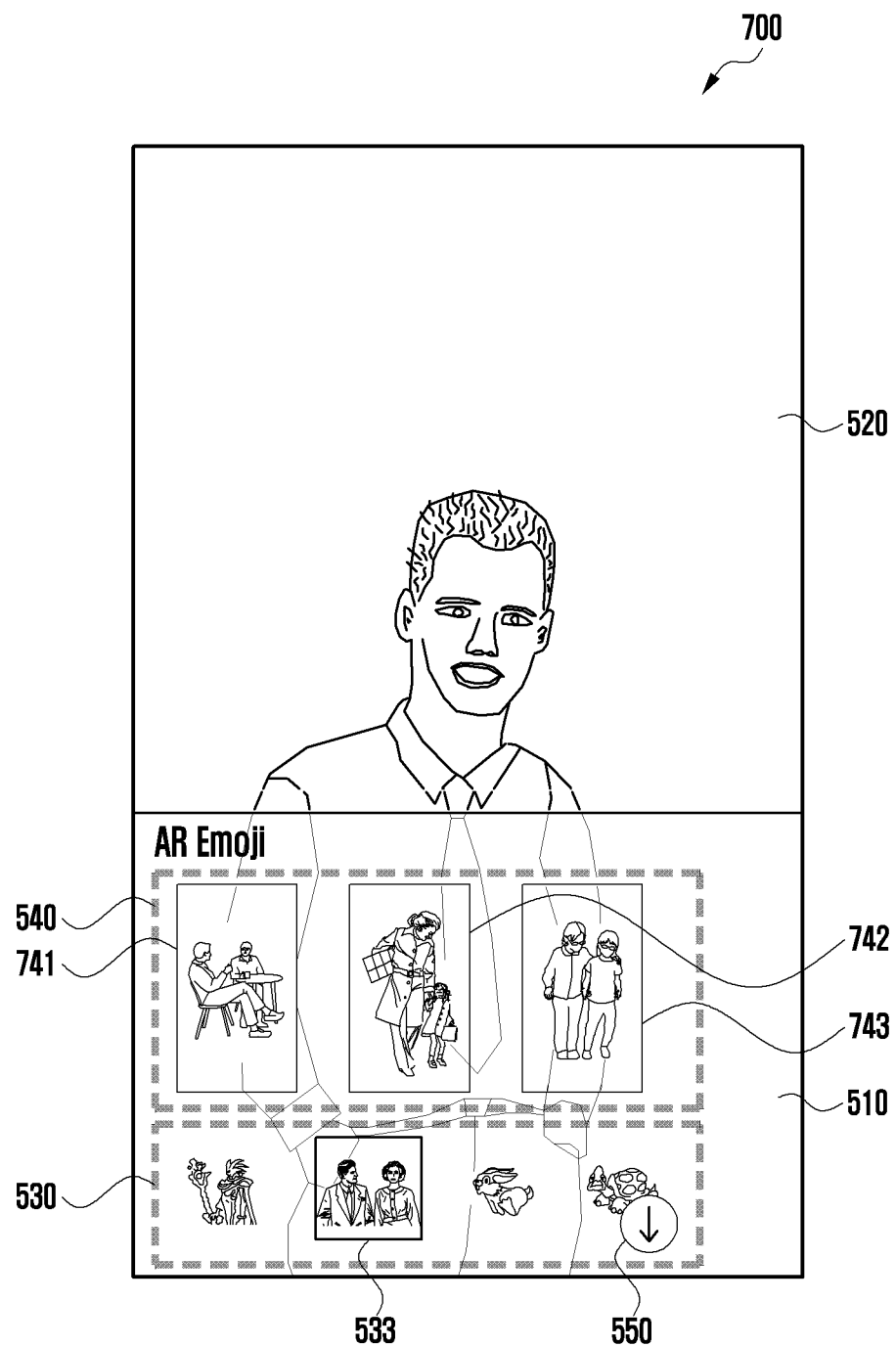
FIG. 7 illustrates a user interface screen supporting display of a downloaded package in avatar camera mode according to certain embodiments.

FIG. 7 illustrates a user interface screen 700 supporting display of a downloaded package in an avatar camera mode, according to certain embodiments. With reference to FIG. 7, when download of the package selected in avatar camera mode is completed, the processor 120 may install the downloaded package in the memory 130, end the display of the download window (e.g., download window 610 in FIG. 6), and display the avatar camera menu 510 on the preview image 520.

Upon completion of download of the selected package, the processor 120 may alter a shape of the corresponding icon to indicate that the download and installation of the selected package is completed. For example, the processor 120 may display the third package icon 533 without an arrow shaped mark 550 (e.g., as with mark 550 in FIG. 5) in the package list 530.

In response to a user input selecting the third package icon 533, the processor 120 may terminate the display of the existing character icons (e.g., character icons 541, 542 and 543 in FIG. 5), and display the icon of the character included in the corresponding package (e.g., fourth character icon 741, fifth character icon 742, or sixth character icon 743) in the character list 540.

Figure 8:
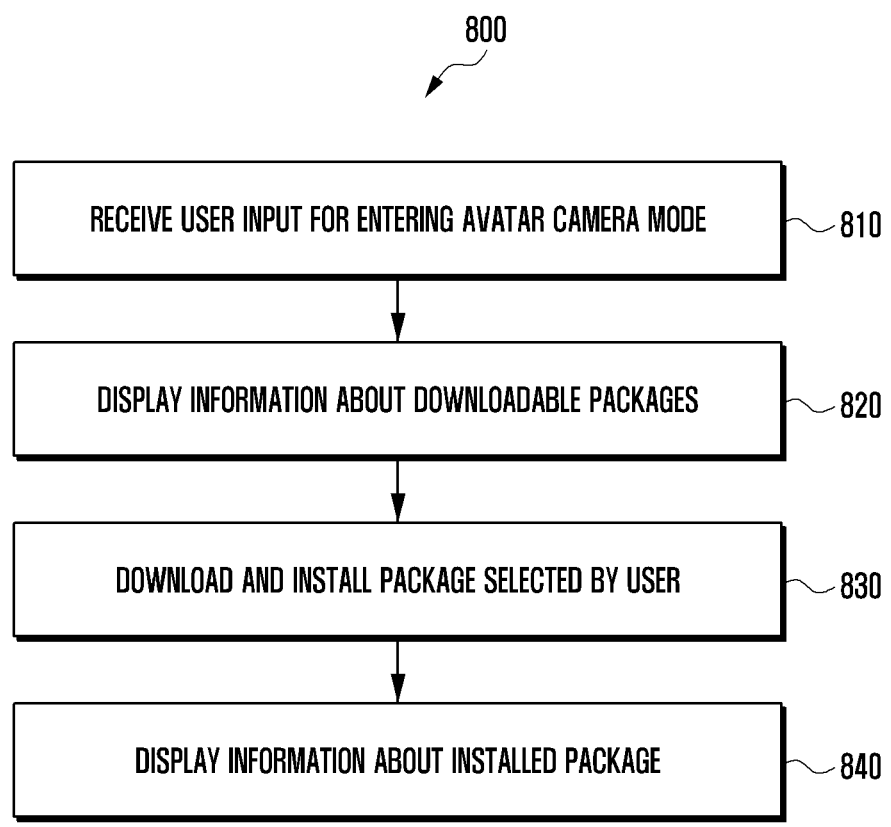
FIG. 8 is a flowchart depicting operations of the processor in avatar camera mode according to certain embodiments.

FIG. 8 is a flowchart depicting operations 800 of the processor 120 in avatar camera mode according to certain embodiments.

At operation 810, the processor 120 may receive a user input for entering avatar camera mode while the preview image is displayed. For example, the processor 120 may obtain an image using the camera module 180, and display the obtained image (or, corresponding low resolution copy image) as a preview image on the display. The processor 120 may display an item selectable to enter the avatar camera mode together with the preview image. The processor 120 may receive a user input selecting the item through the touch screen display.

At operation 820, the processor 120 may display information identifying available downloadable packages, based on a user input received in the avatar camera mode. For example, in response to a user input for entering avatar camera mode, the processor 120 may display an icon representing a downloaded package in the avatar camera menu (e.g. avatar camera menu 510 in FIG. 5). In response to a user input selecting the icon, the processor 120 may retrieve a flag of the package (e.g., character package) corresponding to the selected icon from the memory 130. The processor 120 may transmit the flag to the server 108 through the communication module 190 as a request, and then receive information about the package associated with the flag (e.g., character package having the flag) from the server 108. Based on the received package information (e.g., representative image), the processor 120 may display information about a downloadable package (e.g., third package icon 533 or fourth package icon 534 in FIG. 5) in the avatar camera menu.

At operation 830, the processor 120 may download the package selected by the user as received from the server 108, and install it into the memory 130. For example, the processor 120 may receive a user input for selecting the icon of a downloadable package (e.g., third package icon 533 in FIG. 5). In response to the user input, the processor 120 may display a pop-up window (e.g., download window 610 in FIG. 6) on the display. Based on a user input received through the pop-up window (e.g., user input for selecting the download button 613 in FIG. 6), the processor 120 may download the corresponding package from the server.

At operation 840, the processor 120 may display information identifying the installed package on the display. For example, the processor 120 may display the icon of the downloaded package (e.g., third package icon 533 in FIG. 7) and the icon of a character included in the corresponding package (e.g., fourth character icon 741, fifth character icon 742, or sixth character icon 743 in FIG. 7) on the display.

Figure 9:
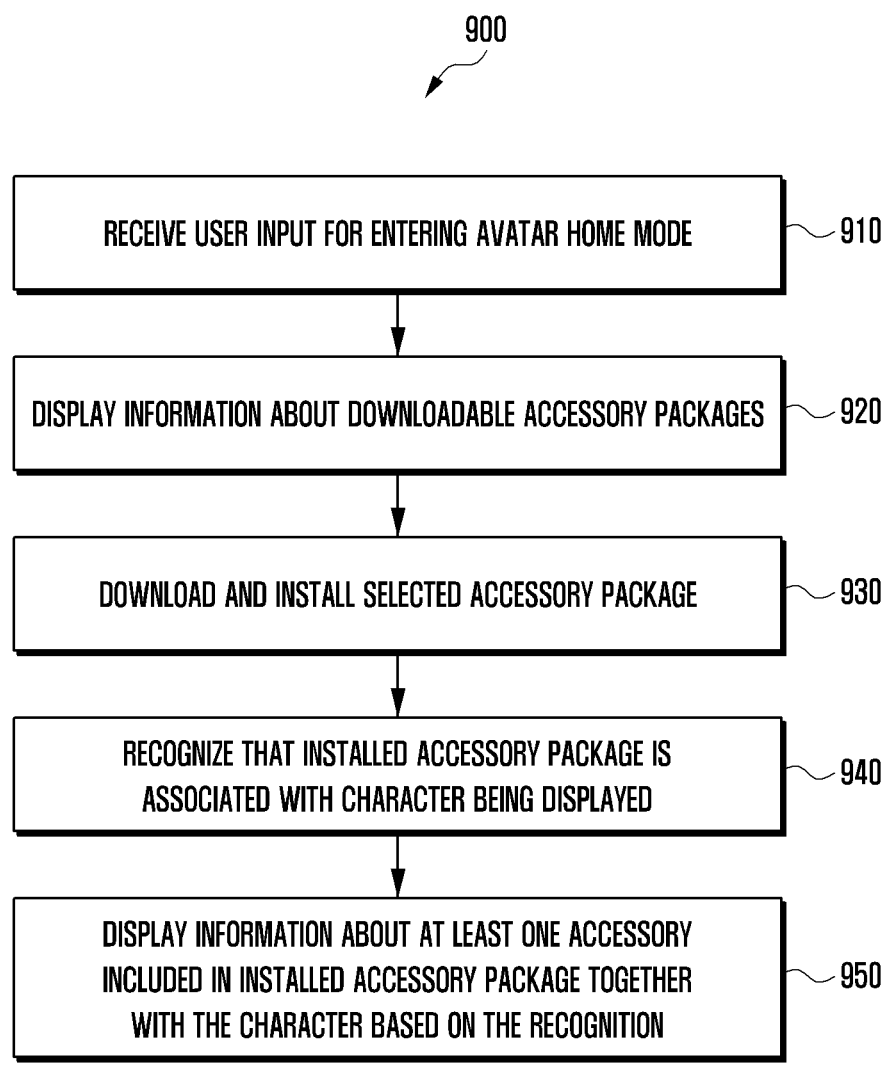
FIG. 9 is a flowchart depicting operations of the processor in avatar home mode according to certain embodiments.

FIG. 9 is a flowchart depicting operations 900 of the processor 120 in avatar home mode according to certain embodiments.

At operation 910, the processor 120 may receive a user input requesting execution of the avatar home mode. For example, the processor 120 may receive a user input selecting the avatar home icon (e.g., icon 580 in FIG. 5) in the avatar camera menu through the display. As another example, the processor 120 may display an icon for entering avatar home mode on the home screen provided by the home application 251. The processor 120 may receive a user input for selecting the avatar home icon on the home screen through the display.

At operation 920, in response to the user input selecting the avatar home icon, the processor 120 may display information identifying downloadable accessory packages (e.g., a plurality of accessory package icons) on the avatar home screen.

At operation 930, the processor 120 may download an accessory package selected by the user from the server 108, and install it into the memory 130.

At operation 940, based on the information identifying the installed accessory package (e.g., accessory package information 480 in FIG. 4), the processor 120 may recognize that the installed accessory package is associated with a character being displayed (e.g., a character potentially selectable as an avatar). For example, the processor 120 may display a character presently selected by the user (e.g. avatar 560 in FIG. 5) on the avatar home screen. The processor 120 may retrieve a package flag (e.g., SAMSUNG Emoji, or Samsung Electronics) corresponding to the character from the memory 130. The processor 120 may recognize that the retrieved package flag matches the flag of the installed accessory package. As another example, the processor 120 may retrieve the flag (e.g., character name) of the character being displayed from the memory 130. The processor 120 may identify an accessory having a matching flag the found character flag from the installed accessory package.

At operation 950, based on the above recognition (e.g., the match between an accessory and a particular character based on the flag metadata), the processor 120 may display information (e.g., accessory icon) about at least one accessory (e.g., hairs, hat, glasses, costume, animation set, or background image) included in the accessory package together with the character on the avatar home screen, thereby ensuring that compatible accessories are provided with any particular character. In an embodiment, the processor 120 may display the icon of a first accessory having a flag identical to the found character flag (e.g., character name) in preference to the icon of a second accessory having a flag different from the found character flag. For example, the processor 120 may display the first accessory icon together with the character on the display without displaying the second accessory icon. In response to a user input for selecting the first accessory icon, the processor 120 may display a character to which the accessory corresponding to the first accessory icon has been applied (e.g., character wearing a hat). As another example, the processor 120 may display both the first accessory icon and the second accessory icon. However, the first accessory icon may be displayed in an enabled state (e.g., distinctively) to visually indicate that it responds to a user input, and the second accessory icon may be displayed in a disabled state (e.g., blurred) to visually indicate that it does not respond to a user input.

Figure 10:
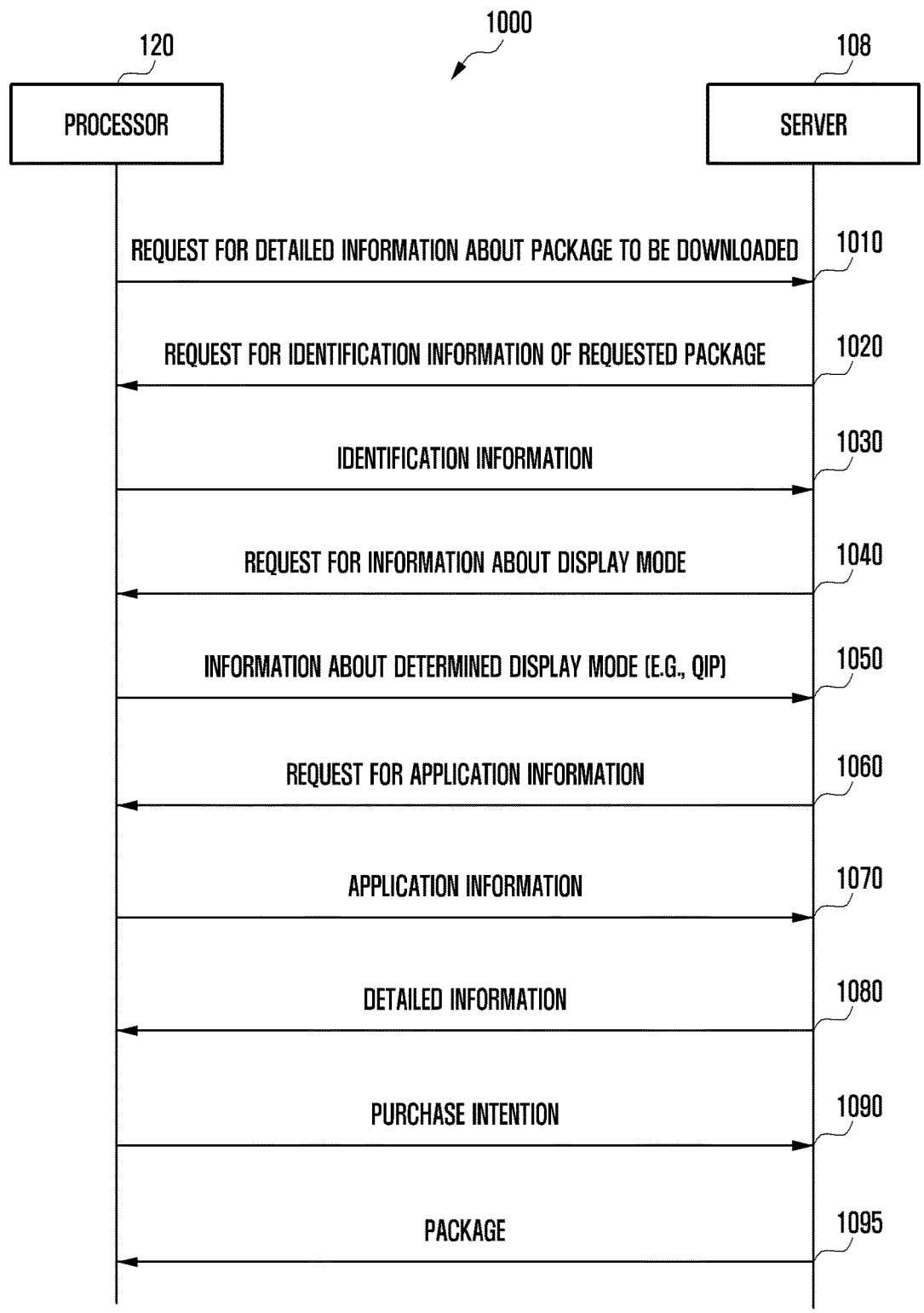
FIG. 10 is a sequence diagram depicting operations between the processor and a server according to certain embodiments.

FIG. 10 is a sequence diagram depicting operations 1000 between the processor 120 and the server 108 according to certain embodiments.

At operation 1010, the processor 120 may connect to the server 108 through the communication module 190 based on a user input and transmit a request message for detailed information about a package to be downloaded to the server 108. For example, in response to a user input for selecting a downloadable package icon (e.g., third package icon 533 in FIG. 5), the processor 120 may transmit a request for detailed information about the corresponding package to the server 108.

At operation 1020, in response to the request from the processor 120, the server 108 may transmit a request message for identification information (e.g., URL or ID of the package) of the requested package to the processor 120.

At operation 1030, in response to the request from the server 108, the processor 120 may transmit identification information of the package to be downloaded to the server 108 through the communication module 190.

At operation 1040, in response to reception of the package identification information, the server 108 may transmit a request message for display mode information of the detailed information to the processor 120.

At operation 1050, in response to the display mode request from the server 108, the processor 120 may determine the display mode to be "display in application" (e.g., quick installation popup (QIP)) based on the user input, and transmit the information about the determined display mode (e.g., values for identifying QIP such as "directClose" and "form") to the server 108 through the communication module 190. For example, predefined display modes for displaying detailed information about a package may include "display in application" and "display in store" (e.g., Galaxy Apps™). In display-in-application mode, detailed information about a package to be downloaded may be delivered through a user interface (e.g., download window 610 in FIG. 6) provided by the running application (e.g., camera application 261 supporting avatar camera mode and/or avatar home mode) without entering a store. In display-in-store mode, detailed information about a package to be downloaded may be delivered through a user interface provided by the corresponding store application. The processor 120 may recognize that the user input having triggered a request for detailed information is a user input utilizing a display-in-application mode (e.g., user's touch input to the third package icon 533 in FIG. 5), and determine the display mode to be "display in application" accordingly.

At operation 1060, in response to reception of the display mode information, to check whether the electronic device 101 includes an application that supports QIP (or is permitted to support QIP), the server 108 may transmit a request message for application information (e.g., predefined permissions, parameters, and other information related to QIP) to the processor 120.

At operation 1070, in response to the request for application information from the server 108, the processor 120 may transmit the requested application information to the server 108 through the communication module 190.

At operation 1080, in response to reception of the application information, the server 108 may transmit the detailed information to the processor 120. Accordingly, the processor 120 may generate a user interface screen (e.g., download window 610 in FIG. 6) based on the received detailed information and display the user interface screen on the display.

At operation 1090, in response to a user input (e.g., touch input to the download button 613 of the download window 610 in FIG. 6), the processor 120 may transmit a purchase intention for the package to the server 108 through the communication module 190.

At operation 1095, in response to the purchase intention, the server 108 may transmit the corresponding package to the processor 120. Accordingly, the processor 120 may notify the user of the download progress by displaying a download progress bar. Upon completion of the download and installation, the processor 120 may display information about the package (e.g., icon) on the avatar camera menu (e.g., avatar camera menu 510 in FIG. 5) or the avatar home screen.

Figure 11:
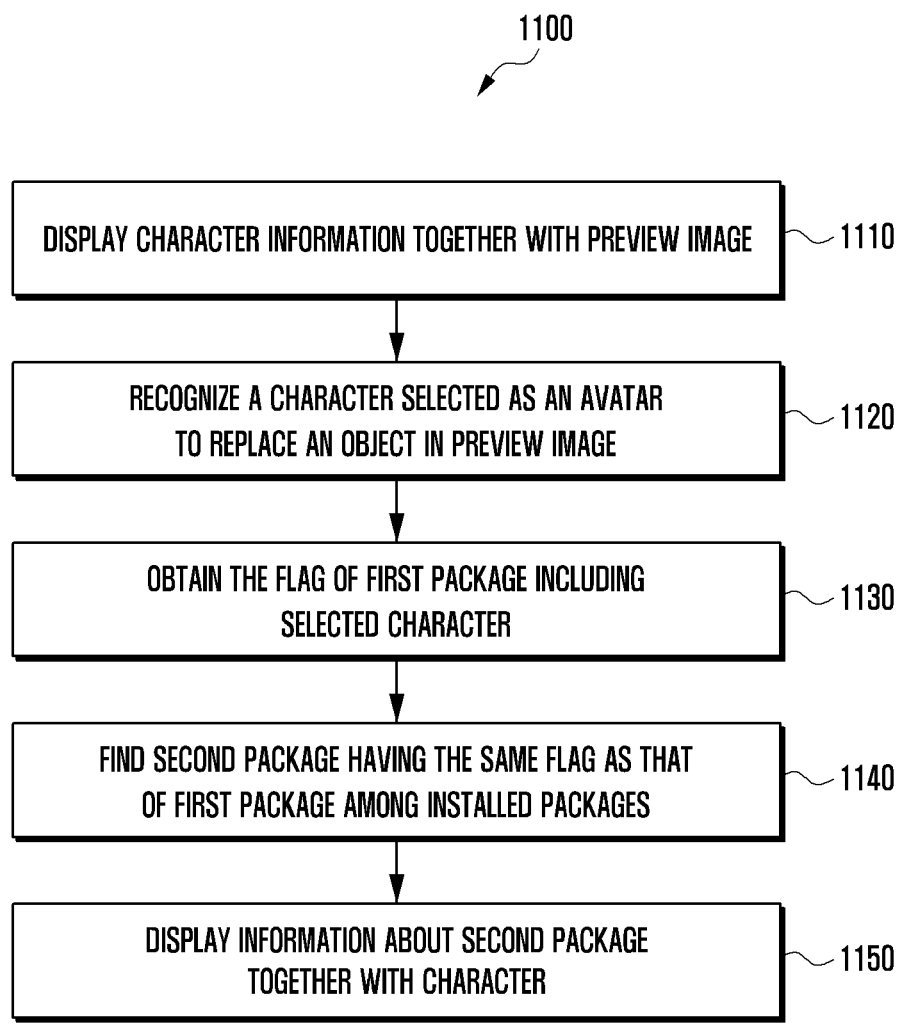
FIG. 11 is a flowchart depicting operations of the processor in avatar camera mode according to certain embodiments.

FIG. 11 is a flowchart depicting operations 1100 of the processor 120 in avatar camera mode according to certain embodiments.

At operation 1110, the processor 120 may display at least one piece of information (e.g., character icon(s)) representing characters together with the preview image on the display.

At operation 1120, based on a user input (e.g., touch input to one of the character icons), the processor 120 may recognize selection of a character as an avatar. In some embodiments, the newly selected avatar may replace a previous displayed object (e.g., a user image) as the preview image.

At operation 1130, the processor 120 may obtain the flag of a first package including the selected character from the memory 130. Additionally, the processor 120 may apply an image processing operation to the selected character and display the processed character in place of the object on the display.

At operation 1140, the processor 120 may retrieve at least one second package (e.g., accessory package) having the same flag as the flag of the first package (e.g., name of the selected character, or holder information such as Samsung Electronics) among the downloaded and installed packages.

At operation 1150, upon detecting that the second package has the same flag as the flag of the first package, the processor 120 may display information identifying the second package together with the character on the display. In an embodiment, the processor 120 may display the icon of the first accessory having the same flag as the name of the selected character in preference to the icon of the second accessory not having the same flag. For example, the processor 120 may display the first accessory icon together with the character without displaying the second accessory icon. As another example, the processor 120 may display the first accessory icon in an enabled state and display the second accessory icon in a disabled state.

According to certain embodiments, there is provided an electronic device. The electronic device may include: an input device; a display including a touch circuit; a camera module; a communication module; a processor operatively connected to the input device, the display, the camera module, and the communication module; and a memory operatively connected to the processor, such that the memory may store instructions that, when executed, cause the processor to: recognize a character selected as an avatar to replace an object included in an image obtained by using the camera module; and display, based on identification information of the character, an icon representing a first package that is downloaded or downloadable and is associated with the character together with the character on the display.

The instructions may be configured to cause the processor to download the first package from an external electronic device through the communication module in response to receiving a user input to the first package icon from the input device or the display.

The instructions may be configured to cause the processor to find the flag of a second package including the character from the memory, and the first package may include the same flag as that of the second package.

The instructions may be configured to cause the processor to display, upon completion of the download of the first package, the first package icon in a visually different manner from before completion of the download (e.g., third package icon 533 displayed without the arrow shaped mark 550 in FIG. 7).

The instructions may be configured to cause the processor to display a package list (e.g., package list 530 in FIG. 5) on the screen including the character, such that the package list may include an icon of the second package including the character, and the first package icon. The instructions may be configured to cause the processor to display, based on the recognition that the first package is not downloaded, the first package icon (e.g., third package icon 533 or fourth package icon 534 in FIG. 5) and the second package icon (e.g., first package icon 531 or second package icon 532 in FIG. 5) in a visually distinguished manner. The instructions may be configured to cause the processor to display a list of characters in the second package on the screen including the character, such that in the character list, the icon of the character may be displayed in a manner visually distinguished from the icon of another character.

The instructions may be configured to cause the processor to: display, based on receiving a user input to the first package icon from the input device or the display, a download window (e.g., download window 610 in FIG. 6) on the screen including the character; and download, based on receiving a user input to a button included in the download window, the first package from the external electronic device. The instructions may be configured to cause the processor to: transmit, based on receiving a user input to the first package icon from the input device or the display, identification information of the first package to the external electronic device; receive a request message for display mode information from the external electronic device as a reply to the first package identification information; transmit, based on the request from the external electronic device, a response message including information indicating that display mode is related to a user interface of a camera application to the external electronic device; and display the download window configured based on information received as a reply for the response message from the external electronic device. The elements of the download window may include at least one of the name of the first package, information on the provider of the first package, a summary description of the first package, an outline of characters included in the package, or a detailed description thereof.

The downloaded first package may include a plurality of accessories and flags corresponding respectively to the accessories, and the instructions may be configured to cause the processor to display an icon of a first accessory having the same flag as the identification information of the character, among the accessories, together with the character (e.g., operation 950). The instructions may be configured to cause the processor to display an icon of a second accessory not having the same flag as the identification information of the character, among the accessories, in a visually different manner from the first accessory icon.

The first package has been downloaded and installed in the memory, and the instructions may be configured to cause the processor to: find a second package flag included in the character from the memory based on the character being displayed in place of the object; recognize that the first package includes a flag identical to the second package flag; and display, based on the recognition, information about the first package together with the character on the display.

According to certain embodiments, there is provided a method for operating an electronic device. The method may include: recognizing a character selected as an avatar to replace an object included in an image obtained by using a camera module; and displaying, based on identification information of the character, an icon of a first package that is downloaded or downloadable and is associated with the character together with the character on a display. The method may further include downloading the first package from an external electronic device through a communication module based on receiving a user input to the first package icon from an input device or the display. When the first package has been downloaded and installed in the memory, the method may further include: finding a second package flag included in the character from a memory based on the character being displayed in place of the object; recognizing that the first package includes a flag identical to the second package flag; and displaying, based on the recognition, information about the first package together with the character on the display.

Hereinabove, certain embodiments of the disclosure have been shown with reference to the accompanying drawings and described for the purpose of illustration without limiting the subject matter of the disclosure. It should be understood by those skilled in the art that many variations and modifications of the basic inventive concept described herein will still fall within the disclosure as defined in the appended claims and their equivalents.

What is claimed is:
1. An electronic device, comprising:
an input circuitry;
a display;
a camera;
a communication circuitry;
a processor operatively connected to the input circuitry, the display, the camera, and the communication circuitry; and
a memory operatively connected to the processor,
wherein the memory stores instructions that, when executed, cause the processor to:
display, on the display, one or more images from among the one or more images depicting characters selectable as avatars;
detect via the input circuitry a selection of a character as an avatar;
set the selected character as the avatar, replacing an object included in an image captured by the camera;
transmit identification information for the selected character to an external electronic device through the communication circuitry;
receive one or more icons representing one or more packages including a first package associated with the selected character from the external electronic device, based on the identification information for the selected character; and display, on the display, the one or more icons representing the one or more packages including the first package associated with the selected character, wherein the one or more icons are displayed before the one or more packages including the first package are downloaded from the external electronic device.

2. The electronic device of claim 1, wherein the instructions are configured to cause the processor to:

download the first package from the external electronic device through the communication circuitry, in response to receiving a selection of a first package icon associated with the first package.

3. The electronic device of claim 2, wherein the instructions are configured to cause the processor to:

retrieve a flag metadata for the character from a second package stored in the memory, wherein the first package is displayed as part of the one or more packages associated with the selected character based on a match between the flag metadata of the character and a flag metadata included in the first package.

4. The electronic device of claim 2, wherein the instructions are configured to cause the processor to:

alter a visual appearance of the first package icon after completing the download of the first package.

5. The electronic device of claim 1, wherein the instructions are configured to cause the processor to:

display a package list on the display, including displaying the character, and the one or more packages associated with the character.

6. The electronic device of claim 5, wherein an icon for the first package of the one or more packages and an icon for a second package of the one or more packages are displayed differently, based on detecting that the first package is not downloaded to the memory and the second package is downloaded to the memory.

7. The electronic device of claim 3, wherein the instructions are configured to cause the processor to:

display a list of characters included within the second package on the display, the displayed list including the selected character, wherein the selected character is displayed with a visual effect to distinguish the selected character from non-selected characters included in the list.

8. The electronic device of claim 2, wherein the instructions are configured to cause the processor to:

based on receiving a selection of the first package icon using the input circuitry, display a download window including the selected character; and in response to receiving a selection of a button displayed in the download window, initiate download of the first package from the external electronic device.

9. The electronic device of claim 8, wherein initiating the download of the first package from the external device includes:

based on receiving a selection of the first package icon from the input circuitry, transmit identification information for the first package to the external electronic device;

receive, from the external electronic device, a reply to the transmitted identification information for the first package including a request for display mode information;

based on the request for the display mode information received from the external electronic device, transmit to the external electronic device a response message including the display mode information indicating a user interface of a camera application; and based on information received from the external electronic device, configure and display the download window.

10. The electronic device of claim 9, wherein the displayed download window being displayed at least one of:

a name associated with the first package, identification of a provider of the first package, a summary of the first package, identification of any characters included in the first package, and a description for each of the characters.

11. The electronic device of claim 2, wherein the downloaded first package includes a plurality of accessories indicating visual effects applicable various characters, and flag metadata each corresponding respectively to each of the accessories, and wherein one or more accessories are selected from among the plurality of accessories for display with the selected character, based on flag metadata of each of the one or more accessories matching flag metadata for the selected character.

12. The electronic device of claim 11, wherein other accessories having flag metadata that fails to match the flag metadata for the selected character are displayed differently with the one or more accessories.

13. The electronic device of claim 2, wherein the instructions are configured to cause the processor to:

after the download, install the first package into the memory;

retrieve a flag metadata from a second package including the character, the second package stored in the memory;

detect whether a flag metadata of the first package matches the flag metadata of the second package; and based on the flag metadata of the first packages matching the flag metadata of the second package, display information associated with the first package with the selected character on the display.

14. A method for operating an electronic device, the method comprising:

displaying, on a display, one or more images depicting characters selectable as avatars;

detecting, using input circuitry, a selection of a character from among the one or more images as an avatar;

setting, by a processor, the selected character as the avatar by replacing an object included in an image captured by a camera of the electronic device;

transmitting identification information for the selected character to an external electronic device;

receiving one or more icons representing one or more packages including a first package associated with the selected character from the external electronic device, based on the identification information for the selected character; and displaying, on the display, the one or more icons representing the one or more packages including the first package associated with the selected character, wherein the one or more icons are displayed before the one or more packages including the first package are downloaded from the external electronic device.

15. The method of claim 14, further comprising:

downloading the first package from the external electronic device using communication circuitry, based on detecting a selection of a first package icon using input circuitry of the electronic device.

16. The method of claim 14, further comprising:
retrieving a flag metadata for the character from a second package stored in a memory,
wherein the first package is displayed as part of the one or more packages associated with the selected character, based on a match between the flag metadata of the character and a flag metadata included in the first package.

17. The method of claim 15, further comprising:
altering a visual appearance of the first package icon after completing the download of the first package.

18. The method of claim 14, further comprising:
displaying a package list on the display, including displaying the character, and the one or more packages associated with the character.

19. The method of claim 18, wherein an icon for the first package of the one or more packages and an icon for a second package of the one or more packages are displayed differently, based on detecting that the first package is not downloaded to a memory and the second package is downloaded to the memory.

20. The method of claim 15, further comprising:
after the download, installing the first package into a memory;
retrieving a flag metadata from a second package including the character, the second package stored in the memory;
detecting whether a flag metadata of the first package matches the flag metadata of the second package; and
based on the flag metadata of the first packages matching the flag metadata of the second package, displaying information associated with the first package with the selected character on the display.

* * * * *